United States Patent
Weispfenning et al.

(10) Patent No.: US 7,840,276 B2
(45) Date of Patent: Nov. 23, 2010

(54) GENERIC DEVICE PROGRAMMER NETWORK INTERFACE

(75) Inventors: Ryan W. Weispfenning, St. Paul, MN (US); Joseph C. Green, Brooklyn Park, MN (US); David A. Furland, Arden Hills, MN (US)

(73) Assignee: Medtronic, Inc., Minneapolis, MN (US)

( * ) Notice: Subject to any disclaimer, the term of this patent is extended or adjusted under 35 U.S.C. 154(b) by 272 days.

(21) Appl. No.: 11/380,301

(22) Filed: Apr. 26, 2006

(65) Prior Publication Data

US 2007/0255597 A1 Nov. 1, 2007

(51) Int. Cl.
*A61N 1/08* (2006.01)

(52) U.S. Cl. .............................. 607/60; 607/32; 128/903

(58) Field of Classification Search ................... 607/30, 607/32, 59, 60; 705/2, 3, 28; 600/509
See application file for complete search history.

(56) References Cited

U.S. PATENT DOCUMENTS

| | | | |
|---|---|---|---|
| 6,250,309 B1 * | 6/2001 | Krichen et al. .............. 128/899 |
| 6,370,433 B1 * | 4/2002 | Hartlaub et al. ................ 607/32 |
| 6,385,593 B2 * | 5/2002 | Linberg ........................ 705/28 |
| 6,418,346 B1 * | 7/2002 | Nelson et al. .................. 607/59 |
| 6,577,901 B2 * | 6/2003 | Thompson ..................... 607/60 |
| 6,580,948 B2 * | 6/2003 | Haupert et al. ................ 607/60 |
| 6,650,939 B2 | 11/2003 | Taepke, II et al. |
| 6,805,667 B2 * | 10/2004 | Christopherson et al. ... 600/300 |
| 2001/0039504 A1 * | 11/2001 | Linberg et al. ................. 705/3 |
| 2003/0074228 A1 * | 4/2003 | Walsh ............................ 705/3 |
| 2004/0117204 A1 * | 6/2004 | Mazar et al. .................... 705/2 |
| 2005/0204026 A1 * | 9/2005 | Hoerl .......................... 709/223 |
| 2006/0015033 A1 * | 1/2006 | Blakley et al. ................. 600/509 |
| 2006/0247709 A1 * | 11/2006 | Gottesman et al. ............ 607/30 |
| 2006/0293604 A1 * | 12/2006 | Carlson et al. ............... 600/509 |

FOREIGN PATENT DOCUMENTS

WO    WO 2007/127623    * 11/2007

* cited by examiner

*Primary Examiner*—Carl H Layno
*Assistant Examiner*—Luther G Behringer

(57) ABSTRACT

A generic device programmer network interface is disclosed. Some embodiments include multiple connectors that are configured to connect to output hardware of multiple programmers and a transmitter that is configured to automatically transmit data received from the programmers to a server. Many embodiments serve to reduce or eliminate barriers to storing IMD and patient data on a server.

14 Claims, 5 Drawing Sheets

GENERIC DEVICE PROGRAMMER NETWORK INTERFACE

BACKGROUND

The present invention relates generally to patient management systems.

Large amounts of medical information can be gathered from patients. Storing such information in a way that all relevant information related to a particular patient is associated with that patient provides numerous benefits. Increasingly, systems dedicated to organizing medical information are becoming electronic. Electronic storage of such information allows larger amounts of information to be stored in less physical space and provides easier and convenient access to such information. These and other factors can allow customers (e.g., physician, nurse, technician, physician's assistant, etc.) who have access to such patient management systems to provide a higher level of care to patients.

In the context of implantable medical devices (IMDs), various IMD data, along with associated patient data, is sometimes stored on a common server. Such IMD data includes information related to parameters such as IMD performance (e.g., device serial number, discrete data, waveform data, etc.) and various physiological indicators of a patient (e.g., heart rhythm, blood pressure, respiration, patient activity level, heart wall motion, blood chemistry, and the like). Various types of IMDs (e.g., cardiac stimulation devices, cardioverters/defibrillators, cardiac monitors, hemodynamic monitors, neuromuscular stimulators, drug delivery devices, or other IMDs) collect and/or store such IMD data. The IMD can transmit such IMD data to the server either directly or, more commonly, indirectly, such as through an external medical device (EMD) (e.g., a programmer or remote home monitor). The EMD can also collect patient data from other sources (e.g., ECG data collected by cables connected directly to a patient) and transmit such patient data to the server. The server then stores the IMD data, along with associated patient data, and provides access to various customers. Creating and maintaining this kind of server can present numerous technical challenges.

DETAILED DESCRIPTION OF ILLUSTRATIVE EMBODIMENTS

The following detailed description of illustrative embodiments should be read with reference to the drawings, in which like elements in different drawings are numbered identically. The drawings depict illustrative embodiments and are not intended to limit the scope of the invention. Rather, the present invention is defined solely by the claims.

Figure 1:
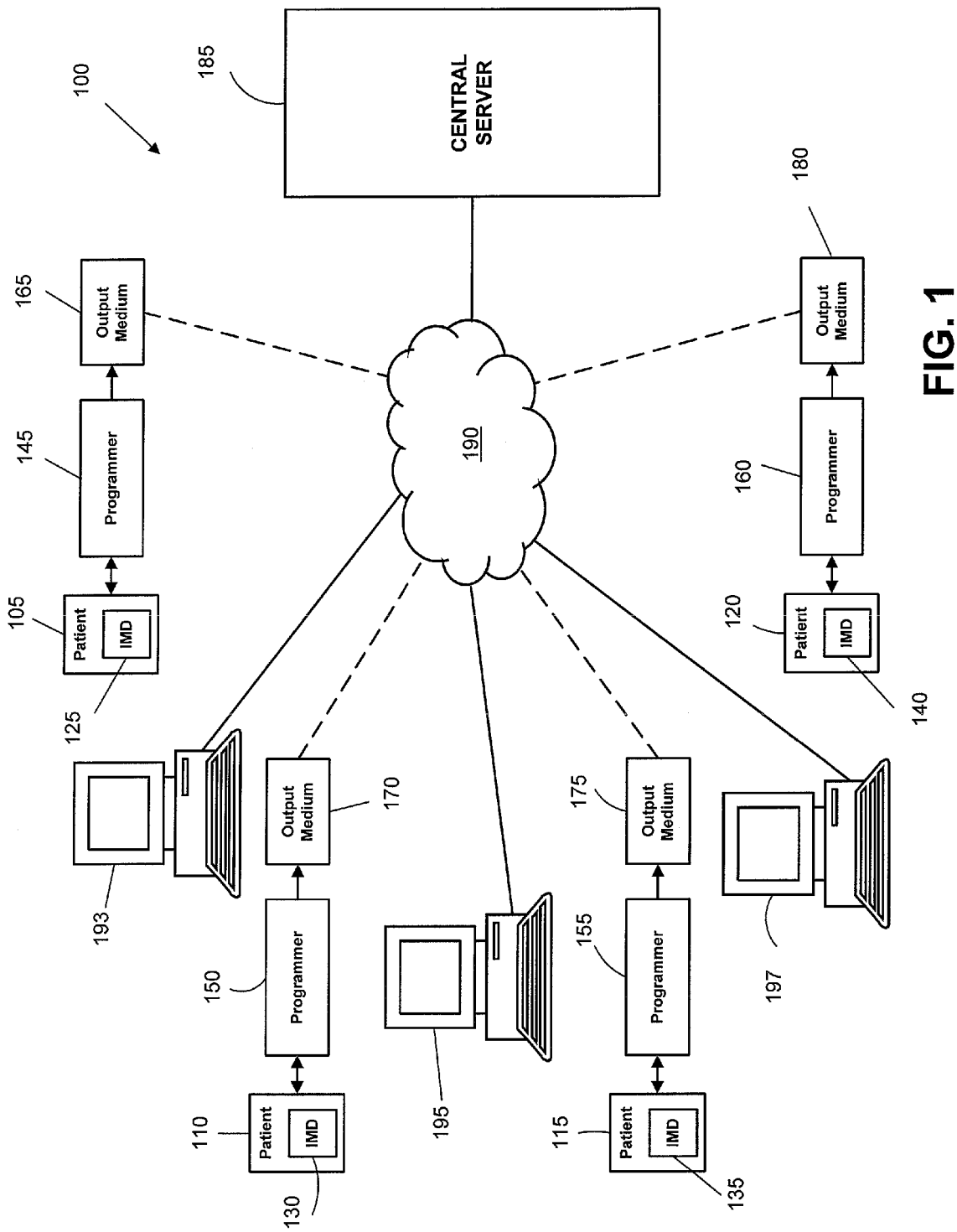
FIG. 1 is a schematic view of an exemplary IMD communication system.

Some embodiments of the invention include the features shown in FIG. 1. FIG. 1 shows an exemplary IMD communication system 100. The IMD communication system 100 is useful for storing, and providing access to, IMD/patient data for multiple patients on a single server. As shown, the IMD communication system 100 involves four patients 105, 110, 115, and 120. However, a greater or lesser number of patients are possible. Each patient 105, 110, 115, 120 has a corresponding IMD 125, 130, 135, 140. In some embodiments, the IMDs 125, 130, 135, 140 differ from one another (e.g., by manufacturer, by type, etc.). That is, IMD 125 may differ from IMD 130, which may differ from IMD 135, which may differ from IMD 140. In one example, IMD 125 is a pacemaker, IMD 130 is an implantable cardiac defibrillator (ICD), IMD 135 is a cardiac monitor, and IMD 140 is a hemodynamic monitor. In another example, all four IMDs 125, 130, 135, 140 are pacemakers, but all are manufactured by a different manufacturer.

The IMD communication system 100 includes programmers 145, 150, 155, 160 to collect IMD/patient data from the IMDs 125, 130, 135, 140 and the patients 105, 110, 115, 120. In some embodiments, the IMD communication system 100 includes one programmer for each IMD and patient. As shown in FIG. 1, programmer 145 corresponds to IMD 125 and patient 105, programmer 150 corresponds to IMD 130 and patient 110, programmer 155 corresponds to IMD 135 and patient 115, and programmer 160 corresponds to IMD 140 and patient 120. In some embodiments, all of the programmers 145, 150, 155, 160 are capable of collecting IMD/patient data from all of the IMDs 125, 130, 135, 140 and all of the patients 105, 110, 115, 120. In some embodiments, some of the programmers 145, 150, 155, 160 are capable of collecting IMD/patient data from some of the IMDs 125, 130, 135, 140 and some of the patients 105, 110, 115, 120. Many additional combinations are possible.

In some embodiments of the IMD communication system 100, the programmers 145, 150, 155, 160 differ from one another (e.g., by manufacturer, by type, etc.). That is, programmer 145 may differ from programmer 150, which may differ from programmer 155, which may differ from programmer 160. For instance, in the example provided above in which all four of the IMDs 125, 130, 135, 140 are pacemakers manufactured by different manufacturers, the four programmers 145, 150, 155, 160 may be manufactured by the four pacemaker manufacturers. In such instances, programmers from a different manufacturer may not be compatible to collect data from IMDs built by another manufacturer.

The programmers 145, 150, 155, 160 of the exemplary IMD communications system 100 collect IMD data from the IMDs 125, 130, 135, 140 through a wireless system such as telemetry antennas. The programmers 145, 150, 155, 160 include a programmer antenna, and the IMDs 125, 130, 135, 140 include an IMD antenna. In some embodiments, the programmer antenna is contained within the programmer 145, 150, 155, 160. In such embodiments, the IMD 125, 130, 135, 140 communicates with the programmer 145, 150, 155, 160 when the programmer 145, 150, 155, 160 is positioned close to the patient's skin overlying the IMD 125, 130, 135, 140. In such embodiments, the IMD patient manually positions the programmer 145, 150, 155, 160 over the IMD 125, 130, 135, 140. In some embodiments, the programmer antenna is located on the case of the programmer 145, 150, 155, 160. In such embodiments, the IMD 125, 130, 135, 140 can communicate with the programmer 145, 150, 155, 160 even when the programmer 145, 150, 155, 160 is located some distance (e.g., several meters) away from the IMD 125, 130, 135, 140. Such embodiments implement long-range telemetry systems. Some telemetry systems allow the IMD 125, 130, 135, 140 to communicate with the programmer 145, 150, 155, 160 without any patient intervention. In other words, as long as the IMD patient is within a communication range of the programmer 145, 150, 155, 160, he or she may be engaged in ordinary activities during a telemetry transmission and may be completely unaware that such transmission is taking place. The IMD/programmer combinations of the exemplary IMD communication system 100 can employ telemetry systems that differ from one another. For example, in certain embodiments, IMDs 125, 130 and corresponding programmers 145, 150 incorporate a manual, short-range telemetry system, while IMDs 135, 140 and corresponding programmers 155, 160 incorporate a long-range, passive telemetry system.

In some embodiments of the exemplary IMD communication system 100, the IMD 125, 130, 135, 140 and the corresponding programmers 145, 150, 155, 160 communicate bi-directionally and in a variety of wireless formats. For example, communication may be via RF. In a transmission from the IMD 145, 150, 155, 160 to the programmer 145, 150, 155, 160 (an uplink telemetry transmission), the IMD antenna operates as a telemetry transmitter antenna, and the programmer antenna operates as a telemetry receiver antenna. Conversely, in a transmission from the programmer 145, 150, 155, 160 to the IMD 125, 130, 135, 140 (an downlink telemetry transmission), the programmer antenna operates as a telemetry transmitter antenna, and the IMD antenna operates as a telemetry receiver antenna. Both the IMD antenna and the programmer antenna can be coupled to a transceiver including a transmitter and a receiver. Often, the communication configuration of programmers manufactured by one manufacturer is incompatible with the communication configuration of IMDs manufactured by a different manufacturer, meaning that such programmers may be unable to collect IMD data from such IMDs.

Some IMD communication systems include multiple programmers that are able to communicate with a given patient's IMD. For example, IMD communication system 100 could include five programmers (not shown), in addition to programmer 145, that are capable of communicating with IMD 125. In such systems, one programmer might be used to collect IMD/patient data from the patient during a first telemetry transmission session, and a different programmer might be used during a second telemetry transmission session.

The IMD communication system 100 includes output media 165, 170, 175, 180 to which programmers 145, 150, 155, 160 provide IMD/patient data. In most embodiments, the programmers 145, 150, 155, 160 do not include sufficient storage to store all relevant IMD/patient data received during multiple telemetry transmission sessions. Thus, in such embodiments, the programmers 145, 150, 155, 160 can either provide such IMD/patient data to separate components (e.g., output media 165, 170, 175, 180) or risk losing it. Maintaining such IMD/patient data in some form generally leads to higher standards of care.

Output media comes in a variety of forms, such as hard copies of documents, electronic files to be stored in various storage media (e.g., floppy disks, CD-ROMs, DVDs, memory sticks, etc.), ECG displays, and other output media. In other words, customers can obtain documents, electronic files, and so on containing the IMD/patient data from the programmer 145, 150, 155, 160. As shown in FIG. 1, programmer 145 corresponds to output medium 165, programmer 150 corresponds to output medium 170, programmer 155 corresponds to output medium 175, and programmer 160 corresponds to output medium 180. In some embodiments, output medium 165 differs from output medium 170, which differs from output medium 175, which differs from output medium 180. Many combinations are possible.

The programmers 145, 150, 155, 160 can include a variety of output hardware capable of providing IMD/patient data to the output media 165, 170, 175, 180. Examples include a parallel port (connected to a printer), a floppy disk drive, a CD-ROM drive, a USB port, an ECG output port, a serial port, and other suitable output hardware. In some embodiments, the output hardware of the programmers 145, 150, 155, 160 prevents the programmers 145, 150, 155, 160 from providing IMD/patient data to certain kinds of output media. For example, programmer 145 might include only a parallel port, which would result in the generation of hard copies of documents but would not result in, e.g., electronic files, ECG displays, or other output media. Similarly, programmer 150 might only include a floppy disk drive, programmer 155 might only include an ECG output port, and programmer 160 might include a serial port.

When a customer prepares to collect IMD data from a patient's IMD, he/she is often faced with a limited selection of programmers that are compatible with that patient's IMD. The programmers that are compatible with that patient's IMD might not be capable of providing the IMD/patient data in that customer's preferred output medium. For example, the customer might want a hard copy of the patient's IMD/patient data, though the available programmers might only be capable of creating electronic files (e.g., when the customer is near a printer, but not near a PC). In another example, the customer could want both a hard copy and an electronic file, though the available programmers might only be capable of providing one or the other. In these and other similar situations, the customer either has to settle for IMD/patient data in a less-than-optimal output medium (which could potentially impede the level of care) or take extra steps to get the IMD/patient data in the preferred output medium (which would consume valuable time and resources).

In some instances, customers do not take advantage of programmers 145, 150, 155, 160 that are capable of outputting to ECG machines. Multiple cables and connectors often must be assembled in order to collect IMD/patient data from the patient and to output such IMD/patient data from the programmer 145, 150, 155, 160 to the ECG machine. This assembly process consumes valuable time and human resources. In such instances, customers often connect a separate sensor to the patient in order to generate an ECG display rather than engaging in the complicated assembly process. Thus, functionality of these kinds of programmers 145, 150, 155, 160 is often under-utilized.

The exemplary IMD communication system 100 includes a central server 185, which stores and provides access to IMD data, along with associated patient data. The central server 185 communicates with the various components of the exemplary IMD communication system 100 via a network 190. The network 190 can be a local area network (LAN), a wide area network (WAN), or other suitable telecommunications network, including the Internet. IMD communication systems could include multiple separate networks. In some embodiments, the central server 185 communicates directly with the various components of the IMD communication system 100.

In some embodiments, difficulties arise in getting the IMD/patient data from the output media 165, 170, 175, 180 to the central server 185 through the network 190. For example, when the programmer 145, 150, 155, 160 generates only a hard copy of a document, the contents of that report often have to be entered manually into the central server 185. Similarly, when the programmer 145, 150, 155, 160 generates only an ECG display (printable or not), the contents of that ECG display have to be entered manually into the central server 185. When the programmer 145, 150, 155, 160 generates only an electronic file, a customer has to take extra steps to load that electronic file onto the central server 185. The extra steps involved with loading IMD/patient data into the central server 185 consume valuable time and energy. Moreover, as the number of patients associated with the central server 185 increases, loading IMD/patient data into the central server 185 can become very difficult administratively. For example, if a customer collects IMD/patient data for 30 patients during a day, making sure all of the reports/data remain identified with the appropriate patients can be cumbersome.

In a small number of embodiments, the programmer 145, 150, 155, 160 communicates directly to the central server 185 through communication components (e.g., network card) housed in the programmer 145, 150, 155, 160. But the majority of embodiments involve programmers 145, 150, 155, 160 that can only communicate to output media 165, 170, 175, 180, thereby requiring extra steps for adding the IMD/patient data from the output media 165, 170, 175, 180 to the central server 185. An important aspect of some embodiments of the present invention is that it equips older programmers, having limited communication functionality, to easily store IMD/patient data on a central server 185, thereby retrofitting such programmers. Because the IMD/patient data is typically not provided automatically by either the programmers 145, 150, 155, 160 or the output media 165, 170, 175, 180 to the central server 185 (either through the network 190 or directly), FIG. 1 shows such connections as dashed lines. Given the many different kinds of programmers, and the many different kinds of output media, creating and maintaining a patient management system such as the IMD communication system 100 often presents difficulties.

The exemplary IMD communication system 100 includes workstations 193, 195, 197. The workstations 193, 195, 197 are able to communicate with the central server 185 through the network 190 in a variety of ways, including both wireless and hardwired communication. In some embodiments, the workstations 193, 195, 197 communicate with the central server 185 through a different network than the network through which IMD/patient data is transmitted to the central server 185. Using the workstations 193, 195, 197, customers are able to access any of the IMD/patient data stored in the central server 185. As such, when a customer is interacting with a particular patient, the customer has access to all of the IMD/patient data for that patient that was ever stored in the central server. This functionality underscores the importance of removing all barriers to storing IMD/patient data on the central server.

In many instances, the customer only wishes to view a portion of the IMD/patient data stored on the central server 185. In such embodiments, the central server 185 or other components can select the IMD/patient data that the customer wishes to view and can provide that IMD/patient data to the customer in a customized format. Receiving customized IMD/patient data allows customers to review, in effect, the patient's entire record, which often leads to an increased level of care. In some embodiments, the workstations 193, 195, 197 provide a web-based interface for customers to access relevant IMD/patient data.

In addition to serving as a portal through which customers can view IMD/patient data, the workstations 193, 195, 197 can be equipped with other useful functionality. For instance, in many embodiments, customers are able to perform several workflow management functions. Examples of workflow management functions that customers can perform using the combination of a workstation 193, 195, 197 and the central server 185 include scheduling appointments with patients, generating reporting letters and other correspondence with patients, generating reports and correspondence for related (referring, implanting, etc.) physicians, generating billing reports or correspondence for payors, and creating other various documentation.

The workstations 193, 195, 197 can be placed in various locations. For instance, in some embodiments, a workstation 193, 195, 197 is placed in every room in which customers interact with patients. In other embodiments, a workstation 193, 195, 197 is placed on a cart and is wheeled to whichever room the customer interacts with the relevant patient. Sometimes, a workstation 193, 195, 197 is placed in a central location, allowing customers to access the IMD/patient data in one room and to interact face to face with patients in another room. Other configurations are possible.

Figure 2:
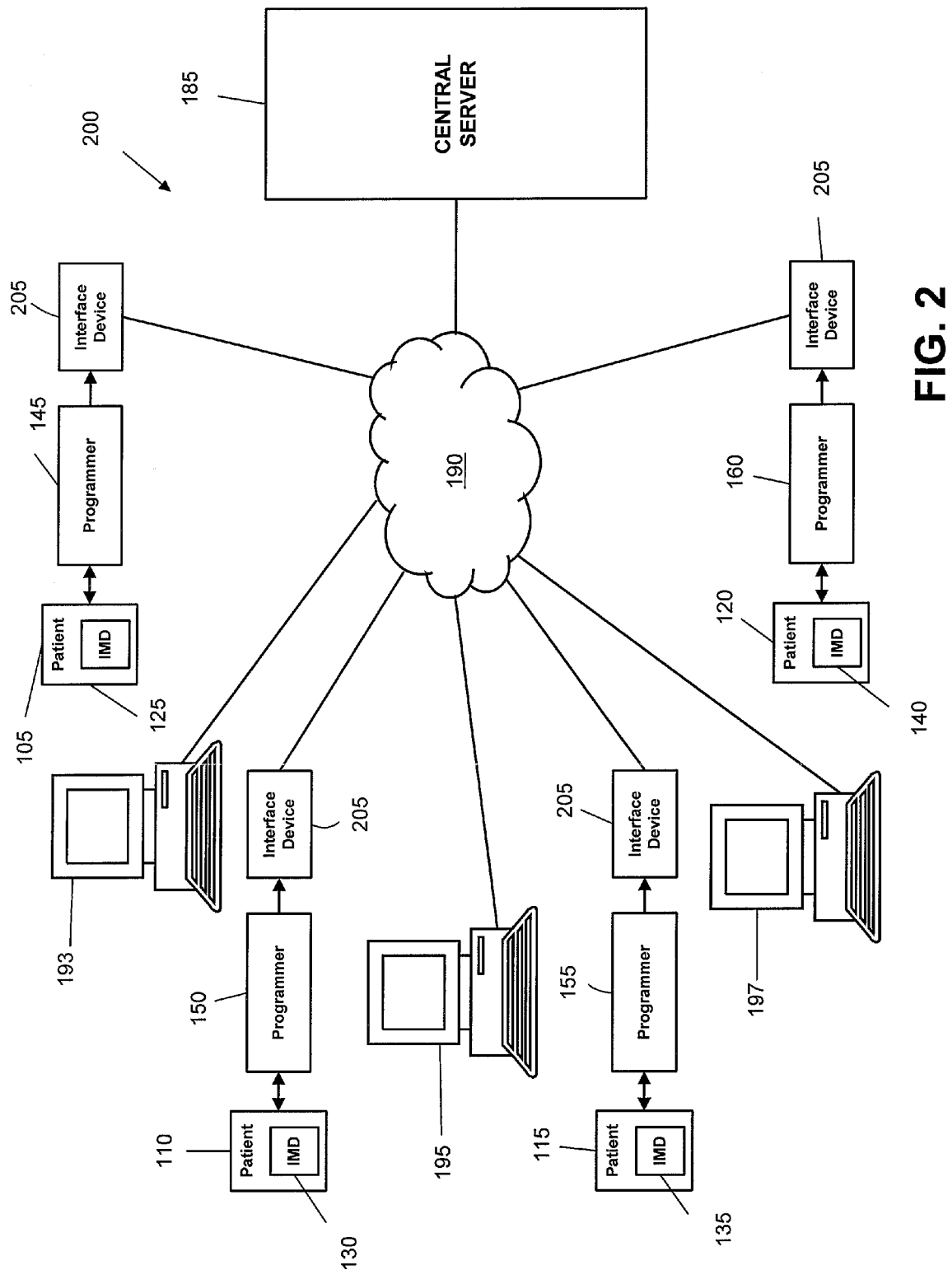
FIG. 2 is a schematic view of a slightly different IMD communication system.

Some embodiments of the invention include the features shown in FIG. 2. FIG. 2 shows an exemplary IMD communication system 200 that is similar to the IMD communication system 100 of FIG. 1. Referring again to FIG. 2, the IMD communication system 200 includes IMDs 145, 150, 155, 160, programmers 165, 170, 175, 180, workstations 193, 195, 197, a network 190, and a central server 185 like those of FIG. 1. Referring again to FIG. 2, the IMD communication system 200 includes multiple interface devices 205, which act as an interface between many different types of programmers and a common central server. Many programmers need not be modified to interact with the interface devices 205. The interface devices 205 are able to receive IMD/patient data from various types of programmers, package that IMD/patient data into a common form, and provide the IMD/patient data to the central server 185 through the network 190. In some embodiments, the interface devices 205 are also able to manipulate the IMD/patient data before providing to the central server 185. The interface devices 205 provide the IMD/patient data to the central server 185 automatically, thereby eliminating the need for customer involvement in loading the IMD/patient data onto the central server 185 (which is why the connection between the interface devices 205 and the network 190 are shown as solid lines). Embodiments of the interface device 205 communicate with the central server 185 in a variety of ways, including both wireless and hardwired communication configurations. With the interface device 205 in place, customers can store all IMD/patient data from the programmers to the central server 185 and choose what to review later rather than choosing what IMD/patient data to store up front.

Thus, the interface devices 205 make it easier to store IMD/patient data from many different IMDs manufactured by a wide range of manufacturers corresponding to numerous patients on the central server 185. This corresponds to customers being able to select from a wider range of IMD/patient data for each patient, which could lead to a higher level of care.

Figure 3:
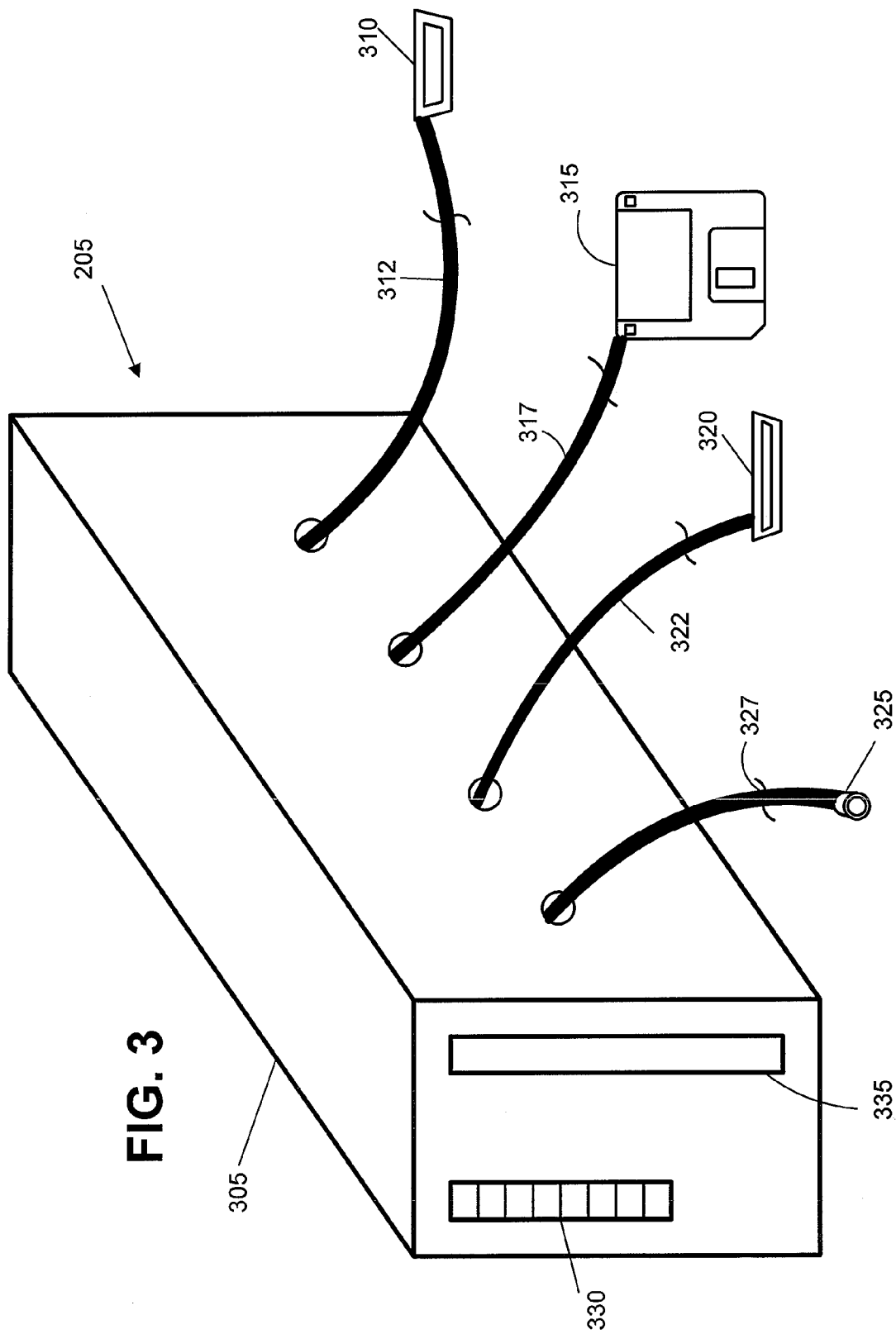
FIG. 3 is a perspective view of an exemplary interface device.
Figure 4:
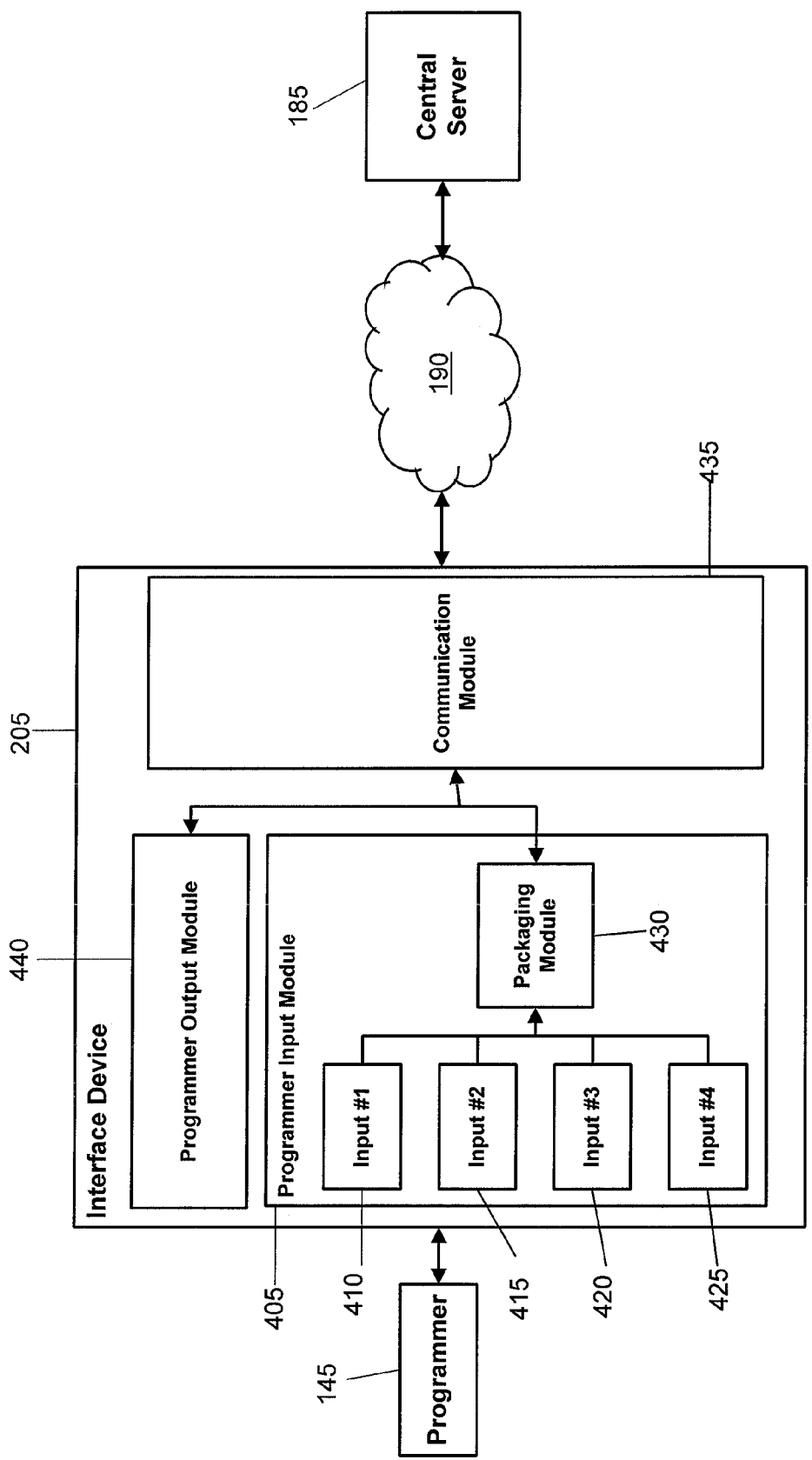
FIG. 4 is a schematic view of a portion of the IMD communication system shown in FIG. 2, with an exemplary interface device shown in greater detail.

Some embodiments of the invention include the features shown in FIGS. 3-4. FIGS. 3-4 illustrate how the interface device 205 of FIG. 2 is configured to interface both physically and logically with almost all programmers. FIG. 3 provides a perspective view of the exemplary interface device 205 referenced in connection with FIG. 2, and FIG. 4 provides a schematic view of the internal logic of the exemplary interface device 205.

Referring to FIG. 3, the interface device 205 includes a housing 305 that, among other things, houses the internal components of the interface device 205. The interface device 205 includes four connectors 310, 315, 320, 325—a serial port connector 310, a floppy disk connector 315, a parallel port connector 320, and an ECG connector 325—that extend from the housing 305 by corresponding cables 312, 317, 322, 327. Some embodiments include different types of connectors, such as a USB connector and/or a CD-ROM connector. Embodiments of the interface device 205 include various combinations of connectors, with some including all six of the connectors discussed herein in some including fewer than six. Other connectors that correspond to other types of programmers can also be included. Customers can select an interface device based on the types of programmers that they regularly encounter.

The connectors 310, 315, 320, 325 enable the interface device 205 to take the place of the various output media discussed elsewhere herein. In other words, the programmer would think it was outputting to an output medium but would actually be outputting to the interface device 205. The serial port connector 310 can be connected to programmers that are configured to output electronic files via serial port, thereby enabling the interface device 205 to receive input from such programmers. The floppy disk connector 315 can be connected to programmers that are configured to output electronic files to floppy disks. The floppy disk connector 315 has the shape of a standard 3.5-inch floppy disk and can be inserted into a programmer's floppy disk drive. The programmer then recognizes the floppy disk connector 315 as a standard floppy disk and writes IMD/patient data in its customary fashion. The floppy disk connector 315 is able to read the IMD/patient data and stream it across the cable to the internal components to be packaged and provided to the central server. The parallel port connector 320 can be connected to programmers that are configured to output IMD/patient data to attached printers for generation of hard copies of documents. In this way, the interface device 205 can receive IMD/patient data from such programmers. The ECG connector 325 can be connected to programmers that are configured to output IMD/patient data to ECG machines thereby enabling the interface device 205 to receive input from such programmers. Because ECG output hardware often varies from programmer to programmer, adapters that are attachable on one end to the ECG connector 325 and on the other end to a particular programmer may also be provided.

A single interface device 205 can work with multiple programmers. The programmers can each be assigned a unique network address. To provide the addressability, the interface device 205 shown in FIG. 3 includes a dip switch 330, but other known addressability mechanisms (e.g., firmware, etc.) can also be provided.

After performing one or more operations to the IMD/patient data (discussed further in connection to FIG. 4), the interface device 205 outputs the IMD/patient data to the central server in a variety of standard ways (e.g., via a wired or wireless PCMCIA Ethernet card). The interface device 205 shown in FIG. 3 includes a network card slot 335 that is configured to receive a network card (e.g., a standard PCMCIA card), which allows the interface device to transmit IMD/patient data from the interface device 205. In some embodiments, the network card slot 335 allows the interface device 205 to adapt to changing protocols of wireless networking. The network card slot 335 could accommodate today, for example, and 802.11g wireless Ethernet PCMCIA card. When a next-generation wireless network emerges, the 802.11g card could be replaced with a newer card that supports the new standard.

FIG. 4 is a schematic diagram showing the exemplary interface device 205 of FIG. 2 in greater detail. Although FIG. 4 shows the interface device 205 as an intermediary between the network 190 and programmer 145, the same interface device 205 can serve as an intermediary between the network 190 and any of the programmers 145, 150, 155, 160 of FIGS. 1-2.

Referring again to FIG. 4, the interface device 205 includes a programmer input module 405, which handles input received from programmer 145. The programmer input module 405 includes multiple inputs 410, 415, 420, 425, which correspond to the varying types of outputs of programmers. For example, input #1 410 could correspond to a parallel port programmer output, which may allow a programmer that is only capable of outputting to a printer through a parallel port to provide IMD/patient data to the interface device 205. In this example, input #1 410 corresponds to the parallel port connector 320 of FIG. 3. Referring again to FIG. 4, in another example, input #2 415 corresponds to a floppy disk programmer output, which allows a programmer that is only capable of outputting to a floppy disk to provide IMD/patient data to the interface device 205. In this example, input #2 415 corresponds to the floppy disk connector 315 of FIG. 3. Referring again to FIG. 4, in a further example, input #3 420 corresponds to an ECG machine programmer output, which allows a programmer that is only capable of outputting to an ECG machine to provide IMD/patient data to the interface device 205. In this example, #3 420 corresponds to the ECG connector 325 of FIG. 3. Referring again to FIG. 4, in another example, input #4 425 corresponds to a serial port programmer output, which allows a programmer that is only capable of outputting to a serial port to provide IMD/patient data to the interface device. In this example, input #4 420 corresponds to the serial port connector 310 of FIG. 3. Referring again to FIG. 4, other examples could include other types of programmers.

In some embodiments of the interface device 205, programmer 145 pushes the IMD/patient data to the programmer input module 405. In some embodiments, the programmer input module 405 pulls the IMD/patient data from programmer 145. In this way, the programmer input module 405 of the interface device 205 can receive IMD/patient data as input from all different kinds of programmers.

The programmer input module 405 of the exemplary interface device 205 includes a packaging module 430. The packaging module 430 receives IMD/patient data from the various inputs 410, 415, 420, 425. In some embodiments, the packaging module 430 pulls the IMD/patient data from the inputs 410, 415, 420, 425. In some embodiments, the inputs 410, 415, 420, 425 push the IMD/patient data to the packaging module 430. The IMD/patient data that the packaging module 430 receives from the inputs 410, 415, 420, 425 can come in various forms. Typically, the packaging module 430 simply packages the IMD/patient data into a form that the central server 185 is capable of understanding (e.g., changing headers, etc.). In some embodiments, the packaging module 430 manipulates the IMD/patient data before sending it on to the central server 185. For example, the packaging module 430 could transmit less than all of the IMD/patient data that it received, based on a particular customer's preferences. Also, in some embodiments, the packaging module 430 performs processes on the IMD/patient data before transmitting it to the central server 185. For example, the IMD/patient data may be analyzed to determine if various criteria are met prior to sending data including, but not limited to: determining if lead impedances have crossed a specified threshold, determining if any new episodes have occurred since the last follow-up, determining if an electrical error has occurred in the IMD, or determining the battery status of the IMD. At a more technical level, the criteria might also include checksum or Cyclic Redundancy Check (CRC) verification, length counts, or other similar checks.

The exemplary interface device 205 includes a communication module 435, which handles communication between the interface device 205 and the central server 185 through the network 190. The communication module 435 receives IMD/patient data in a common format from the packaging module 430. In some embodiments, the communication module 435 pulls the IMD/patient data from the packaging module 430. In some embodiments, the packaging module 430 pushes the IMD/patient data to the communication module 435. The communication module 435 then provides the IMD/patient data to the central server 185 through the network 190 for organization and storage.

In embodiments in which the packaging module 430 receives waveform data from the inputs 410, 415, 420, 425, the packaging module 430 can trigger the central server 185 to begin recording such waveform data. In such embodiments, when the packaging module 430 detects waveform data, it can cause the communication module 435 to generate and transmit a control signal to the central server 185, instructing the central server 185 to begin recording. At an appropriate time (e.g., at the end of a telemetry transmission session), the packaging module 430 can cause the communication module 435 to generate and transmit a control signal to the central server 185, instructing the central server 185 to cease recording. In this way, the functionality of programmers having the capability of outputting to an ECG machine can be fully utilized, and customers can pull desired waveform data from the central server 185. Additional embodiments are possible where the interface device could provide a user interface (e.g. record and stop buttons, etc.) instead of automatically detecting.

The exemplary interface device 205 provides for bi-directional communication between the programmer 145 and the central server 185. The interface device 205 includes a programmer output module 440 to transmit communications from the interface device 205 to the programmer 145. In some embodiments, the programmer 145 includes functionality to provide a more thorough analysis of IMD/patient data than the central server 185. If the customer desires analysis that only the programmer 145 can provide, the central server 185 can transmit essentially raw IMD/patient data to the programmer 145 through the communication module 435 and the programmer output module 440 of the interface device 205. This would allow the programmer 145 to conduct the thorough analysis and provide the analyzed IMD/patient data to the customer, e.g., through one of the output media discussed elsewhere herein.

The interface device 205 shown in FIG. 4 includes several components. Interface devices may include a greater or lesser number of components than those shown. In some interface device embodiments, the functions performed by multiple components in the interface device 205 discussed herein are combined into fewer components, such as one component. In one example, the multiple functions performed by the packaging module 430 and the communication module 435 discussed herein are performed by a single component designed to package IMD/patient data and provide it to the central server. In some interface device embodiments, the functions performed by one component in the interface device 205 discussed herein are performed by multiple components. For example, the multiple functions of the packaging module 430 discussed herein can be performed by a component designed to perform processes on the IMD/patient data, a component designed to package the IMD/patient data, and/or other miscellaneous components. Some interface device embodiments include additional components to provide additional functionality. Components of interface devices can perform the functions discussed herein in various ways. The ways by which the components of the interface device 205 discussed herein are provided only for illustration.

Referring back to FIG. 2, in many embodiments, when customers set out to collect IMD/patient data from a patient, they are equipped with a cart that carries the requisite equipment. The cart often carries one of each of the programmers that correspond to IMDs that such customers regularly encounter. In some embodiments, the cart also carries a single interface device 205, which the customer connects to the appropriate programmer before collecting the IMD/patient data. In many embodiments, the cart carries pre-assembled programmer/interface device combinations. The pre-assembled programmer/interface device combinations eliminate the step of the customer connecting the interface device 205 with the appropriate programmer before collecting the IMD/patient data, thereby potentially saving valuable time.

Figure 5:
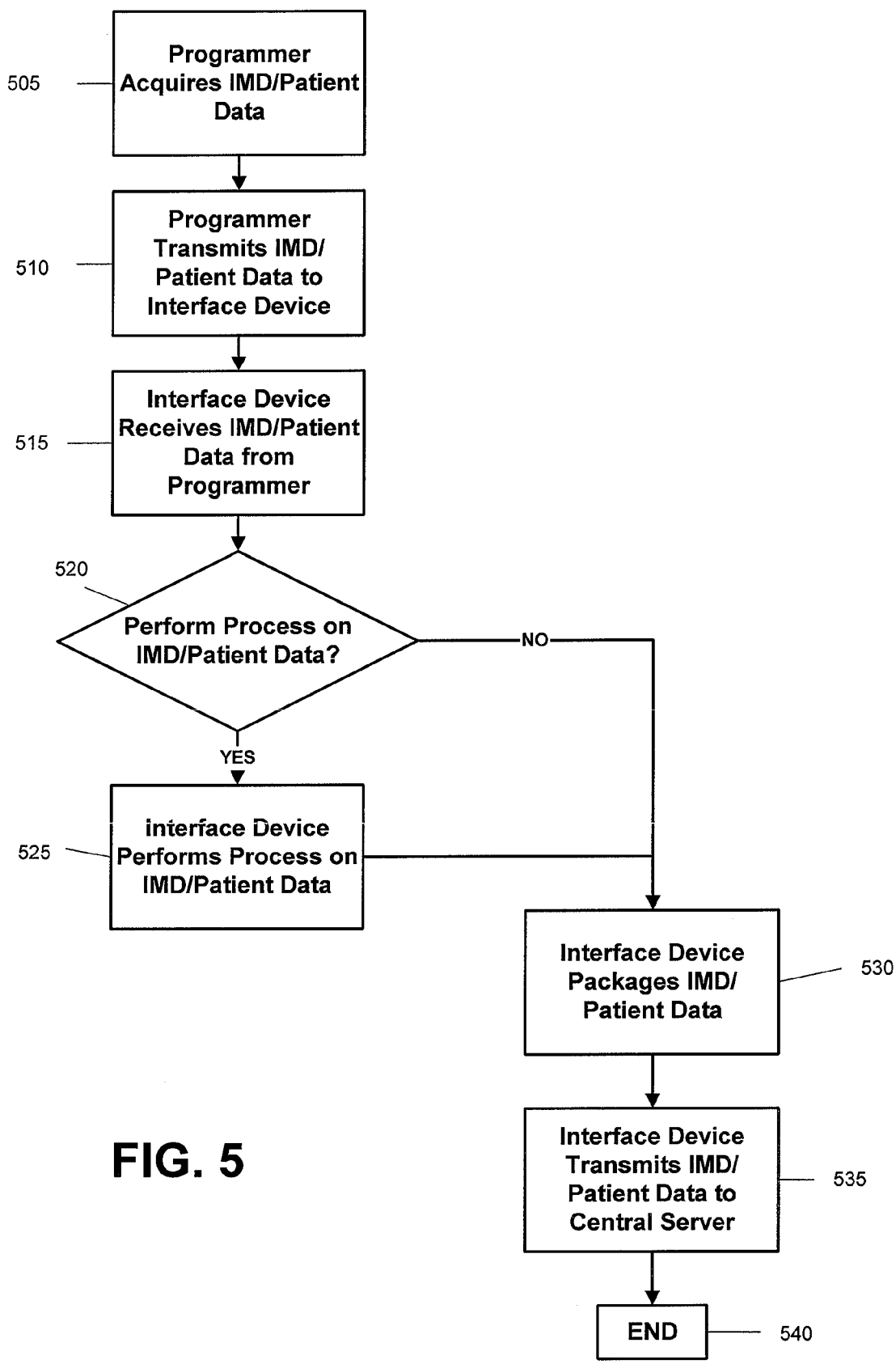
FIG. 5 is a flow chart of an exemplary method that can be implemented in connection with some embodiments of the present invention.

FIG. 5 shows an exemplary method that can be implemented in connection with some embodiments of the present invention. A programmer can acquire IMD/patient data (505) from an IMD implanted within a patient, from other sensors connected to the patient, or from other sources. The programmer transmits IMD/patient data to the interface device (510) in any of the ways discussed elsewhere herein or in any other suitable way. The interface device receives the IMD/patient data from the programmer (515), irrespective of the type of output medium to which the programmer typically outputs. The interface device determines whether to perform a process on the IMD/patient data (520). If the interface device determines that it should perform a process on the IMD/patient data (e.g., based on customer preference), the interface device proceeds to perform that process (525). Whether the interface device performs a process on the IMD/patient data or not, the interface device packages the IMD/patient data (530) for transmission. The interface device transmits the IMD/patient data to the central server (535) in any of the ways discussed elsewhere herein or in any other suitable way, and the method of FIG. 5 comes to an end (540).

The order of steps provided in the methods shown in FIG. 5 is provided for purposes of illustration only, and other orders that achieve the functionality recited are within the scope of the present invention. Further, any of the functionality discussed anywhere in this disclosure may be implemented in the method shown in FIG. 5.

Embodiments of the present invention may have one or more of the following advantages. Some embodiments reduce barriers to storing IMD/patient data on a central server. Some embodiments allow many different kinds of programmers to provide IMD/patient data to a central server automatically, thereby retrofitting older programmers with more modern functionality. Some embodiments allow customers to utilize more of a programmer's functionality. Some embodiments allow customers to view IMD/patient data in their preferred output medium, irrespective of the type of programmer used. Some embodiments allow customers to store all IMD/patient data initially and choose what to review later, rather than choosing what to store up front. Some embodiments allow customers to use one programmer for one telemetry transmission session and a different programmer for a different session while still having access to all of that patient's IMD/patient data. Some embodiments allow for the elimination of redundant connections between components of the system. Some embodiments allow customers to remotely operate the workstation or server from the programmer. Some embodiments reduce the duplication of data entry.

Thus, embodiments of the present invention are disclosed. One skilled in the art will appreciate that the present invention can be practiced with embodiments other than those disclosed. The disclosed embodiments are presented for purposes of illustration and not limitation, and the present invention is limited only by the claims that follow.

The invention claimed is:

1. An interface device for use in a patient management system to serve as an intermediary between a programmer and a server, comprising:
   a housing;
   a first connector extending from the housing via a first cable, the first connector being configured to interface physically with a first output hardware of a first programmer, which is configured to wirelessly collect data from a first implanted medical device, and to receive data collected from the first implanted medical device from the first programmer;
   a second connector extending from the housing via a second cable, the second connector being configured to interface physically with a second output hardware of the first programmer, and to receive data collected from the first implanted medical device from the first programmer, the second output hardware differing from the first output hardware;
   a transmitter in the housing, the transmitter being configured to automatically transmit data received by the first and second connectors to the server.

2. The interface device of claim 1, wherein the transmitter is configured to transmit data according to a wireless protocol.

3. The interface device of claim 2, wherein the transmitter includes an upgradeable feature to allow the transmitter to transmit data according to a first wireless protocol at a first time and according to a second wireless protocol at a second later time.

4. The interface device of claim 1, wherein the first and second output hardware are selected from the group consisting of a parallel port, a floppy disk drive, a CD-ROM drive, a USB port, an ECG output port, and a serial port.

5. The interface device of claim 1, further comprising third and fourth connectors extending from the housing via third and fourth cables,
   the third connector being configured to interface physically with a third output hardware of the first programmer, and to receive data collected from the first implanted medical device from the first programmer, the third output hardware differing from the first and second output hardware, and
   the fourth connector being configured to interface physically with a fourth output hardware of the first programmer, and to receive data collected from the first implanted medical device from the first programmer, the fourth output hardware differing from the first, second, and third output hardware, the transmitter being configured to automatically transmit data received by the first, second, third, and fourth connectors to the server.

6. The interface device of claim 5, wherein the first, second, third, and fourth output hardware are selected from the group consisting of a parallel port, a floppy disk drive, a CD-ROM drive, a USB port, an ECG output port, and a serial port.

7. The interface device of claim 1, wherein the first connector includes an ECG connector and the transmitter includes a configuration to cause the server to record waveform data.

8. The interface device of claim 1, wherein the transmitter includes a configuration to transmit data to the first connector.

9. The interface device of claim 1, further comprising means for associating the interface device with a network address.

10. The interface device of claim 1, further comprising a processor configured to perform a process on data received by the first and second connectors before the transmitter sends processed data to the server.

11. The interface device of claim 1, wherein the first connector includes a floppy disk connector shaped like a standard 3.5-inch floppy disk.

12. The interface device of claim 1, wherein the first connector is further configured to interface physically with an output hardware of a second programmer in a subsequent operation, the second programmer being configured to wirelessly collect data from a second implanted medical device, and to receive data collected from the second implanted medical device from the second programmer.

13. An interface device for use in a patient management system to serve as an intermediary between a programmer and a server, comprising:
   a housing;
   a first connector extending from the housing via a first cable, the first connector being configured to interface physically with a first output hardware of the programmer, which is configured to wirelessly collect data from a implanted medical device, and to receive data collected from the implanted medical device from the programmer;
   a second connector extending from the housing via a second cable, the second connector being configured to interface physically with a second output hardware of the programmer, which is configured to wirelessly collect data from the implanted medical device, and to receive data collected from the implanted medical device from the programmer;
   a third connector extending from the housing via a third cable, the third connector being configured to interface physically with a third output hardware of the programmer, which is configured to wirelessly collect data from the implanted medical device, and to receive data collected from the implanted medical device from the programmer;
   a fourth connector extending from the housing via a fourth cable, the fourth connector being configured to interface physically with a fourth output hardware of the programmer, which is configured to wirelessly collect data from the implanted medical device, and to receive data collected from the implanted medical device from the programmer; and
   a transmitter housed in the housing, the transmitter being configured to automatically transmit data received by the first, second, third, and fourth connectors to the server, the first, second, third, and fourth output hardware being different from one another.

14. The interface device of claim 13, wherein the first, second, third, and fourth output hardware are selected from the group consisting of a parallel port, a floppy disk drive, a CD-ROM drive, a USB port, an ECG output port, and a serial port.

* * * * *